(12) United States Patent
Westlund

(10) Patent No.: US 7,197,362 B2
(45) Date of Patent: Mar. 27, 2007

(54) CARDIAC LEAD HAVING COATED FIXATION ARRANGEMENT

(75) Inventor: Randy Westlund, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/733,868

(22) Filed: Dec. 11, 2003

(65) Prior Publication Data

US 2005/0131511 A1 Jun. 16, 2005

(51) Int. Cl.
*A61N 1/05* (2006.01)
(52) U.S. Cl. ................................. 607/127; 607/121
(58) Field of Classification Search ........ 607/126–131, 607/116, 122, 121; 600/375
See application file for complete search history.

(56) References Cited

U.S. PATENT DOCUMENTS

| 4,010,758 | A | * | 3/1977 | Rockland et al. ........... 607/131 |
|---|---|---|---|---|
| 4,313,448 | A | * | 2/1982 | Stokes ....................... 607/130 |
| 4,357,946 | A | * | 11/1982 | Dutcher et al. ............ 607/131 |
| H000356 | H | * | 11/1987 | Stokes et al. ............... 607/126 |
| 5,139,033 | A | | 8/1992 | Everett et al. |
| 5,143,090 | A | * | 9/1992 | Dutcher et al. ............ 607/121 |
| 5,342,628 | A | * | 8/1994 | Picha ......................... 424/484 |
| 5,391,200 | A | | 2/1995 | KenKnight et al. |
| 5,545,201 | A | * | 8/1996 | Helland et al. ............. 607/127 |
| 5,551,427 | A | * | 9/1996 | Altman ....................... 600/374 |
| 5,609,622 | A | | 3/1997 | Soukup et al. |
| 5,728,140 | A | * | 3/1998 | Salo et al. ...................... 607/9 |
| 5,845,396 | A | * | 12/1998 | Altman et al. ................ 29/885 |
| 5,931,862 | A | * | 8/1999 | Carson ....................... 607/120 |
| 6,324,415 | B1 | * | 11/2001 | Spehr et al. ................ 600/374 |
| 6,501,994 | B1 | * | 12/2002 | Janke et al. ................ 607/127 |
| 2002/0147486 | A1 | | 10/2002 | Soukup et al. |

OTHER PUBLICATIONS

P. Karpawich, H. Walters and M. Hakimi. "Chronic Performance of a Transvenous Steroid Pacing Lead Used as an Epi-Intramyocardial Electrode." Children's Hospital of Michigan, Detroit, Michigan. Jul. 1998, PACE vol. 21, pp. 1486-1488.

* cited by examiner

*Primary Examiner*—Jeffrey R. Jastrzab
(74) *Attorney, Agent, or Firm*—Hollingworth & Funk, LLC

(57) ABSTRACT

Implantable cardiac monitoring and stimulation devices and methods using cardiac leads employ coated fixation arrangements. The coating, such as an expanded polytetrafluoroethylene, reduces exit block by reducing the tissue response to the fixation arrangement, decreasing the amount of fibrotic tissue, and reducing exit block. An epicardial lead may include a lead body with one or more electrical conductors with associated insulators and an electrode assembly situated at the distal end. The electrode assembly includes an electrode having an active fixation arrangement such as a helical fixation element. The fixation arrangement is completely or partially coated with a fluoropolymer or has a sleeve on some or all of the active fixation arrangement. The coating or sleeve may include a steroid or other pharmacological eluting arrangement disposed on the active fixation arrangement.

35 Claims, 4 Drawing Sheets

CARDIAC LEAD HAVING COATED FIXATION ARRANGEMENT

FIELD OF THE INVENTION

The present invention relates generally to leads for implantable cardiac monitoring and stimulation devices and, more particularly, to electrodes and methods for implanting cardiac leads having coated fixation arrangements.

BACKGROUND OF THE INVENTION

Rhythmic contractions of a healthy heart are normally controlled by the sinoatrial (SA) node that includes specialized cells located in the superior right atrium. The SA node is the normal pacemaker of the heart, typically initiating 60–100 heartbeats per minute. When the SA node is pacing the heart normally, the heart is said to be in normal sinus rhythm (NSR).

The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways can suffer compromised cardiac output, such as that associated with congestive heart failure, for example.

Cardiac rhythm management devices have been developed that provide pacing stimulation to one or more heart chambers in an attempt to improve the rhythm and coordination of atrial and/or ventricular contractions. Cardiac rhythm management devices may incorporate defibrillation and/or pacemaker circuitry used to treat patients with serious arrhythmias. Cardiac rhythm management devices typically include circuitry to sense signals from the heart and a pulse generator for providing electrical stimulation to the heart. One or more leads are typically delivered transvenously or transthoracicly into the heart, and are coupled to electrodes that contact the myocardium for sensing the heart's electrical signals and for delivering stimulation to the heart in accordance with various therapies. Cardiac rhythm management devices may deliver low energy electrical pace pulses timed to assist the heart in producing a contractile rhythm that maintains cardiac pumping efficiency appropriate to meet the metabolic requirements of the patient.

While transvenous lead delivery is appropriate for many patients that experience adverse synchronization conditions, there are a significant number of patients who could benefit from cardiac resynchronization therapy or other cardiac stimulation therapies, but are not good candidates for transvenous surgical procedures. Many of these patients are considered poor candidates for transvenous lead implantation for various reasons, including inability to locate the coronary sinus, presence of coronary sinus stenosis, inability to catheterize a desired branch vein, instability of the transvenous lead, or unacceptably high pacing threshold, for example.

SUMMARY OF THE INVENTION

The present invention is directed to implantable cardiac monitoring and stimulation devices and methods using cardiac leads having coated fixation arrangements. A coating, such as an expanded polytetrafluoroethylene (ePTFE), for example, reduces exit block by reducing the tissue response to the fixation arrangement, decreasing the amount of tissue fibrosis, and reducing exit block development.

An epicardial lead in accordance with the present invention includes a lead body with one or more electrical conductors with associated insulators. An epicardial electrode assembly is situated at the distal end of the lead body. The electrode assembly includes an electrode having a fixation arrangement such as, for example, a helical fixation element. The fixation arrangement is completely or partially coated with a fluoropolymer or includes a sleeve on some or all of the fixation arrangement.

The lead may also incorporate a polymeric coating disposed on at least the fixation arrangement, and include a fluoropolymer coating or sleeve disposed over the polymeric coating. The fluoropolymer coating or sleeve may be manufactured from, for example, polytetrafluoroethylene (PTFE) or ePTFE. The coating or sleeve may include a steroid or other pharmacological eluting arrangement disposed on the fixation arrangement.

An endocardial lead in accordance with the present invention includes a lead body with one or more electrical conductors with associated insulators. An endocardial electrode assembly is situated at the distal end of the lead body and includes at least one helical electrode, typically an extendable/retractable electrode. The helical electrode is completely or partially coated with a fluoropolymer or includes a sleeve on some or all of the fixation arrangement. The coating or sleeve may include a steroid or other pharmacological eluting arrangement disposed on the helical electrode.

According to another embodiment of the present invention, a method of implanting an epicardial lead on a patient's heart involves accessing, via a patient's chest cavity, an epicardial surface of the heart. An electrode assembly of an epicardial lead is moved to an implant site on the epicardial surface. The electrode assembly includes an electrode having a fixation arrangement, such as, for example, an active fixation arrangement, with a fluoropolymer coating or sleeve provided on some or all of the fixation arrangement. The method further involves implanting the electrode into myocardial tissue at the implant site by use of the fixation arrangement.

The lead may also include a polymeric coating disposed on at least the fixation arrangement, and may include a fluoropolymer coating or sleeve disposed over the polymeric coating. The method may further involve delivering a pharmacological agent from a coating or sleeve, such as a steroid or other pharmacological agent delivered by a pharmacological eluting arrangement disposed on the fixation arrangement.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
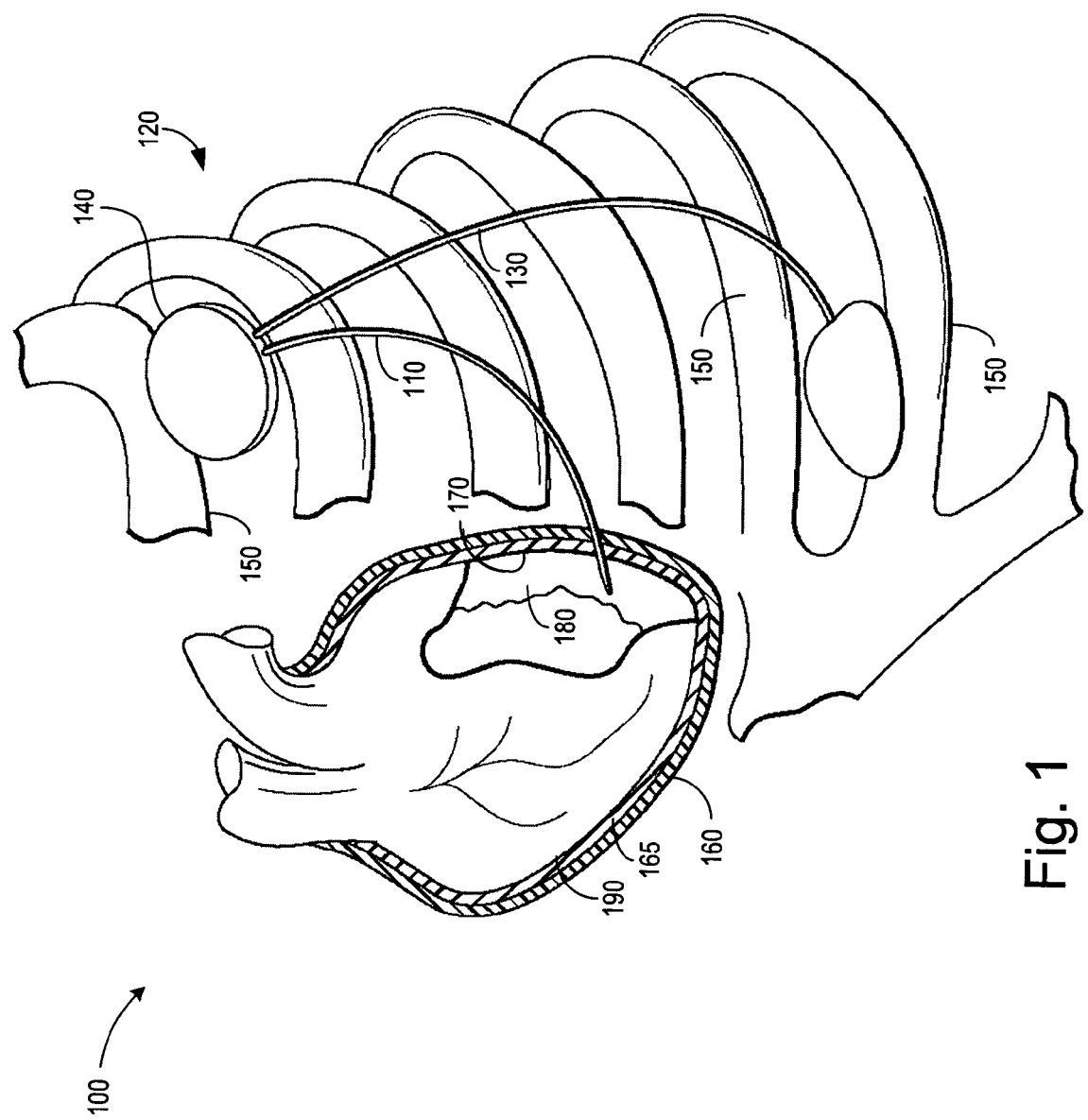
FIG. 1 illustrates a cardiac monitoring and/or stimulation device in accordance with the present invention, as implanted in a patient.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

Methods and devices employing an implantable cardiac monitoring and stimulation device in accordance with the present invention may incorporate one or more of the features, structures, methods, or combinations thereof described herein below. For example, devices and/or leads having coated fixation arrangements may be implemented to include one or more of the features and/or processes described below. It is intended that such a device or method need not include all of the features and functions described herein, but may be implemented to include selected features and functions that, alone or in combination, provide for unique structures and/or functionality.

Leads and systems in accordance with the present invention that incorporate coated fixation arrangements may be used with epicardial lead placement, endocardial lead placement, and/or intramyocardial lead placement. Epicardial lead placement usually involves a mini-thoracotomy, providing access for a lead that is screwed into the myocardial tissue at the desired wall location. However, heart failure studies of epicardial leads of the prior art have been subject to scrutiny due to the development of exit block. Exit block is a condition where fibrotic tissue encapsulates the epicardial lead's electrode. This encapsulation drives up pacing thresholds, sometimes to the point of system failure.

FIG. 1 illustrates a cardiac monitoring and/or stimulation system 100 in accordance with the present invention, as implanted in a patient. In general terms, a lead 110 implemented in accordance with the present invention may be used with a cardiac monitoring and/or stimulation device providing a system with reduced exit block. One such device is an implantable cardiac monitoring and/or stimulation (ICMS) device 120 that includes a housing or can 140 implanted under the skin in the abdominal or chest region of a patient.

The can 140 of the ICMS device 120 may be configured for positioning outside of the rib cage at an intercostal or subcostal location, within the abdomen, or in the upper chest region and include one or more leads 110 having one or more electrodes implanted within myocardial tissue of the heart. Although a single lead 110 is shown implanted in the left ventricle in FIG. 1, it is understood that one or more leads 110 may be implanted in myocardial tissue of one or more chambers of the heart, or that other leads, such as, for example, endocardial leads, may be used in combination with one or more leads 110.

The lead 110 shown in FIG. 1 is connected to the can 140 of the ICMS device 120. The can 140 is positioned external of the patient's rib cage 150. The lead 110 extends from the can 140, through the intercostal space, and into the thoracic cavity. The lead 110 penetrates the pericardium 160. An electrode of the lead 110 penetrates the epicardium 170 and is implanted in the myocardium 180 of the heart 190.

The ICMS device 120 may also be used with other leads, such as, for example, a subcutaneous lead 130. The subcutaneous lead 130 may be used for monitoring and/or stimulation in combination with one or more of the lead(s) 110. For example, subcutaneous leads that may be used in cooperation with the ICMS system 100 are disclosed in commonly owned U.S. Publication No.2004/0230230, which is hereby incorporated herein by reference. One or more leads 100 may further be used in combination with a subcutaneous monitoring and/or stimulation device of the type disclosed in commonly owned U.S. Publication No. 2004/0230229, which is hereby incorporated herein by reference.

The ICMS device 120 shown in FIG. 1 is intended to be representative of various types of cardiac rhythm management devices. Such devices include, for example, implantable pulse generators such as pacemakers and implantable cardioverter/defibrillators that provide electrical stimulation to selected chambers of the heart. A pacemaker, for example, is an implantable pulse generator that paces the heart with timed pacing pulses. A common condition for which pacemakers are used is in the treatment of bradycardia, where the ventricular rate is too slow. Atrio-ventricular conduction defects (i.e., AV block) that are permanent or intermittent and sick sinus syndrome represent common causes of bradycardia for which permanent pacing may be indicated. If functioning properly, the pacemaker makes up for the heart's inability to pace itself at an appropriate rhythm in order to meet metabolic demand by enforcing a minimum heart rate.

Another embodiment of the ICMS device 120 is a cardiac resynchronization device, which monitors and regulates the degree to which the heart chambers contract in a coordinated manner during a cardiac cycle to effect efficient pumping of blood. The heart has specialized nerve conduction pathways in both the atria and the ventricles that enable the rapid conduction of excitation waveforms throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency may be greatly diminished. Patients who exhibit pathology of these conduction pathways, such as bundle branch blocks, can thus suffer compromised cardiac output.

Heart failure, for example, is a clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF may be due to a variety of etiologies, with ischemic heart disease being the most common. Some CHF patients suffer from some degree of AV block or are chronotropically deficient such that their cardiac output may be improved with conventional bradycardia pacing. Such pacing, however, may result in some degree of uncoordination in atrial and/or ventricular contractions due to the way in which pacing excitation is spread throughout the myocardium. The resulting diminishment in cardiac output may be significant in a CHF patient whose cardiac output is already compromised. Intraventricular and/or interventricular conduction defects (e.g., bundle branch blocks) are also commonly found in CHF patients.

ICMS device 120 may be configured to treat these problems, such as by providing electrical pacing stimulation to one or both ventricles in an attempt to improve the coordination of ventricular contractions, termed cardiac resynchronization therapy. The ICMS device 120 may be configured structurally and functionally in a manner described in commonly owned U.S. Pat. Nos. 6,597,951; 6,574,506; 6,512,952; 6,501,988; 6,411,848; and 6,363,278, each of which is hereby incorporated herein by reference.

Figure 2:
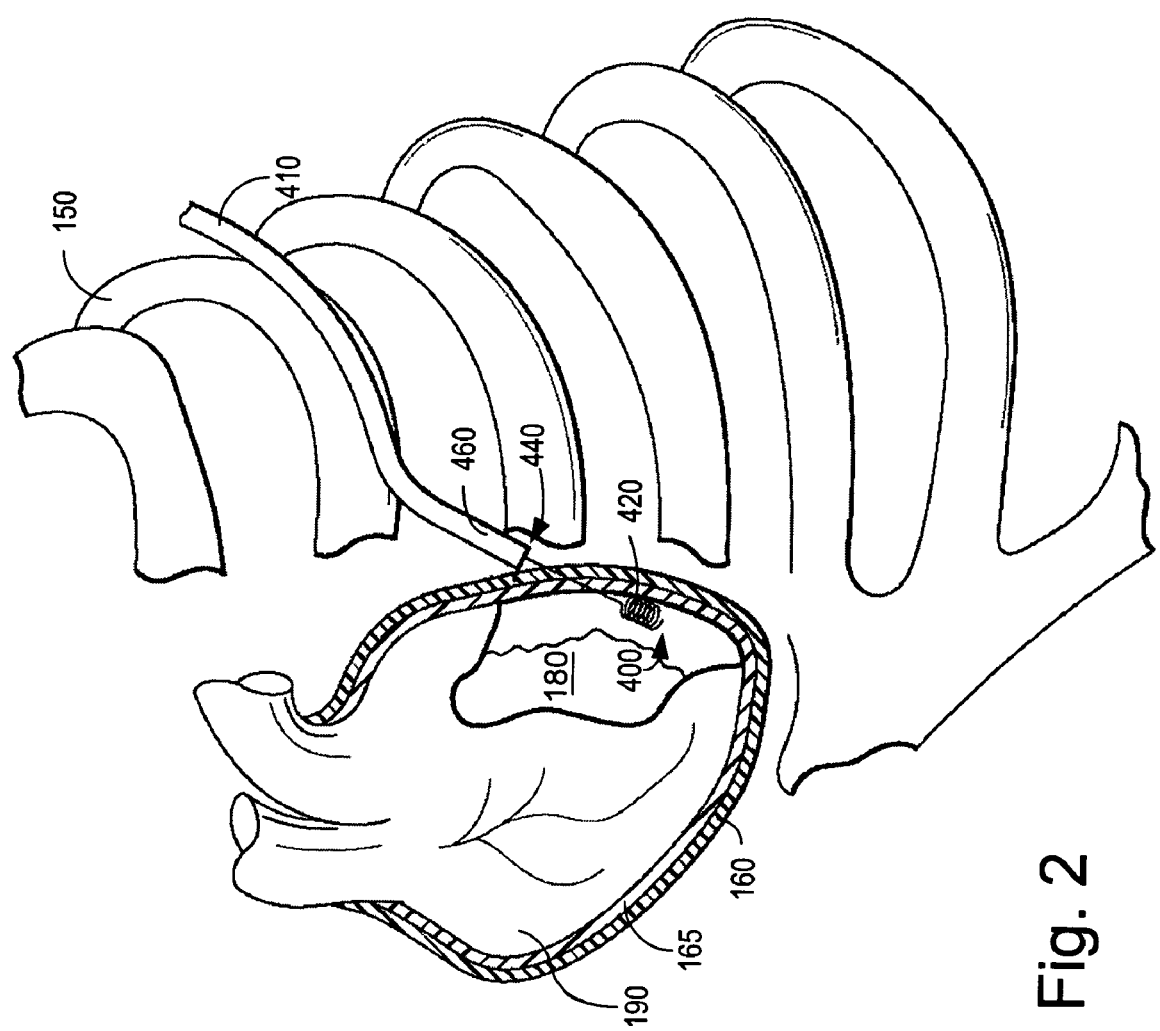
FIG. 2 illustrates a lead having a coated helical fixation arrangement in the myocardium in accordance with an embodiment of the present invention.

Turning now to FIG. 2, there is illustrated a lead 410 having a helical electrode 420 implanted in the myocardium 180 in accordance with an embodiment of the present invention. During delivery of the lead 410, the electrode 420 is implanted within the myocardium 180 by rotating the lead 410. In another embodiment, the electrode 420 may be inserted into the myocardium 180 and actively extended out from the lead and into myocardial tissue, as will be discussed in more detail with reference to FIG. 4 below.

Still referring to FIG. 2, as the lead 410 is rotated, the sharp end 400 of the helical electrode 420 engages myocardial tissue and penetrates into the myocardium 180. As the lead 410 is further rotated, the sharp end 400 burrows through the tissue, penetrating further into myocardial tissue and acutely fixing the electrode within the myocardium 180. This process effectively screws the helical electrode 420 into the myocardial tissue.

Although helical electrode 420 is illustrated having uniform pitch, cylindrical cross-section, and constant coil thickness, it is contemplated that any helical or screw-like structure may be used in accordance with the present invention. The helix may be of non-uniform and/or tapering cross-section, the pitch may be non-uniform, and the shape and thickness of the coil may be varied, for example.

Figure 3A:
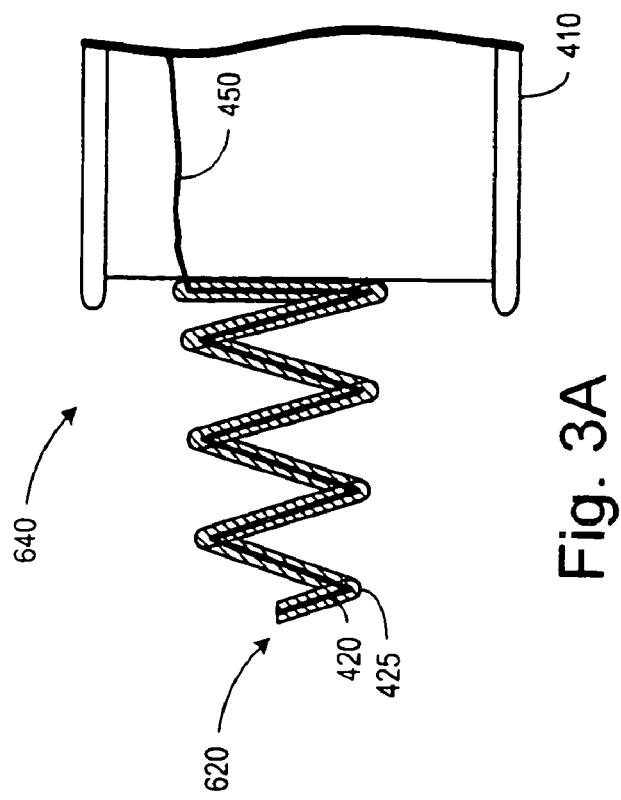
FIGS. 3A and 3C illustrate magnified views of the distal portion, identified in FIG. 3B, of embodiments of a lead having a coated helical fixation arrangement in accordance with the present invention.
Figure 3B:
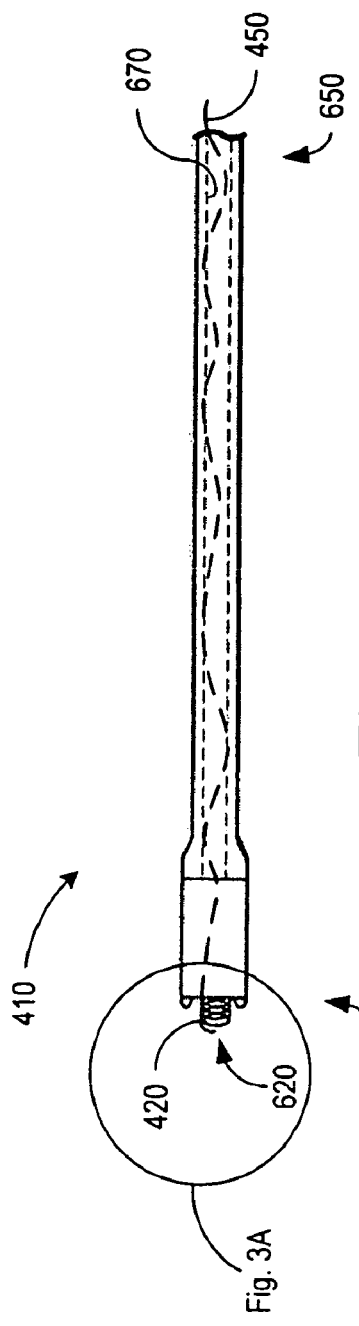
FIG. 3B illustrates a lead in accordance with the present invention, identifying the magnified portion illustrated in FIGS. 3A and 3C.

Referring now to FIGS. 3A and 3B, the lead 410 includes an electrical conductor 450 that is electrically insulated from surrounding tissue through its length and terminates in the distal, pace/sense helical electrode 420. The helical electrode 420 is adapted to be rotated and screwed into the myocardium during the introduction and fixation process as described above. The lead 410 may be an epicardial lead as described above or, in another embodiment, may be configured as an endocardial lead used for transvenous lead implantation. Electrodes and fixation arrangements in accordance with the present invention may be combined with leads such as, for example, those disclosed in commonly assigned U.S. Pat. No. 5,496,362, which is hereby incorporated herein by reference.

An endocardial lead in accordance with the present invention may have, for example, the helical electrode 420 formed of fine platinum-iridium alloy wire having a diameter of about 0.006 inches that is drawn into a helix of a diameter between about 0.027 and about 0.058 inches. Dimensions other than those previously recited are also contemplated. The helical electrode 420 provides contact and attachment with the heart wall at a selected site within the heart chamber.

The conductor 450 is contained within an insulating sheath 670 of lead 410. The conductor 450 may be formed of an electrically insulated multi-strand cable or helical coil of materials typically used in pace/sense lead conductors, such as MP35N alloy having an overall diameter of about 0.003 to about 0.020 inches. Due to the small diameter, a more radio-opaque metal, e.g. platinum-iridium alloy helical coil or a silver core wire multi-strand cable, may be used to enhance visibility under fluoroscopy. The conductor 450 of the pace/sense lead 410 may be encased within a sheath 670 of silicone rubber or a dielectric fluoropolymer material, e.g. PTFE, ETFE or THV200. In the latter case, the sheath 670 may have a wall thickness of about 0.006 inches. The outer diameter of lead 410 is typically on the order of about 0.027 inches or 2 French for the unipolar epicardial pace/sense lead illustrated in FIG. 2.

Figure 3C:
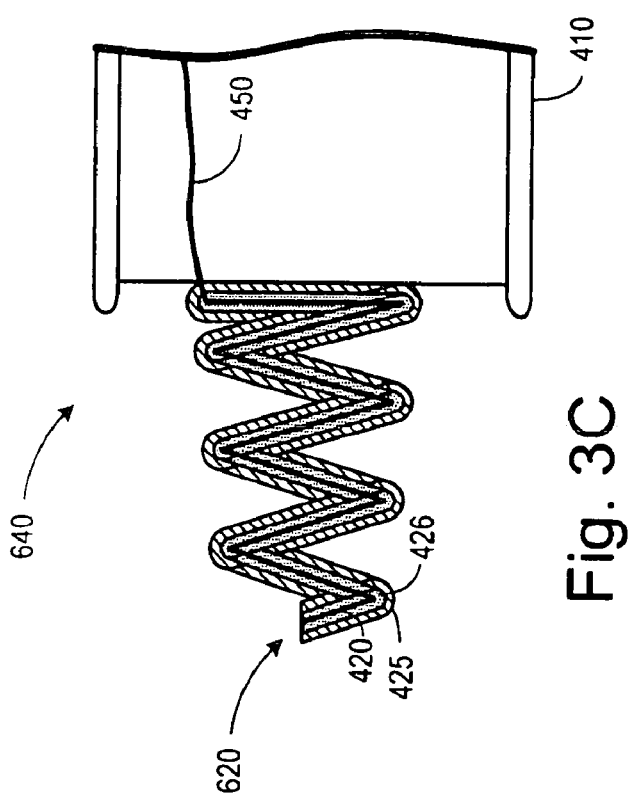

Referring to FIG. 3A, the helical electrode 420 includes a polymer layer 425. The polymer layer 425 may be a coating or sheath, such as, for example, silicon tubing, a PTFE or ePTFE coating, or other layer adapted to reduce the tissue body response to the helical electrode 420. The polymer layer 425 thereby typically covers most or all of the exposed helical electrode 420, but may alternately include voids, apertures, or other discontinuities. The polymer layer 425 solicits less tissue inflammation and reduces the amount of fibrotic tissue around the implant site, reducing exit block development. As illustrated in FIG. 3C, the lead 410 may also incorporate a polymeric coating 426 disposed on at least the fixation arrangement 420, and include a fluoropolymer coating or sleeve 425 disposed over the polymeric coating 426. The fluoropolymer coating or sleeve 425 may be manufactured from, for example, polytetrafluoroethylene (PTFE) or ePTFE. The coating or sleeve 425 may include a steroid or other pharmacological eluting arrangement disposed on the fixation arrangement 420.

In one particular configuration, the sheath 670 may be manufactured from a first polymer material including a first type of PTFE, and the polymer layer 425 may be manufactured from a second polymer material including a second type of PTFE. In one particular arrangement, the first type of PTFE includes a first type of ePTFE, and the second type of PTFE includes a second type of ePTFE. The second type of ePTFE may differ from the first type of ePTFE in terms of one or more of porosity, pore sizes or distribution of pore sizes. Selection of appropriate pore sizes, for example, using a second type of ePTFE at a pore size of less than about 20 microns on the polymer layer 425, provides a reduced body response for the area surrounding the helical electrode 420. Providing a first type of ePTFE at a pore size of greater than about 20 microns on the lead 410 may provide an increased body response. The increased body response may result in chronic fixation of that portion of the lead 410 having the first type of ePTFE.

Additional details of fixation approaches involving surface texturing, selective material use, and other arrangements that facilitate lead fixation via tissue ingrowth are disclosed in commonly owned U.S. Pat. No. 6,691,621.

Figure 4:
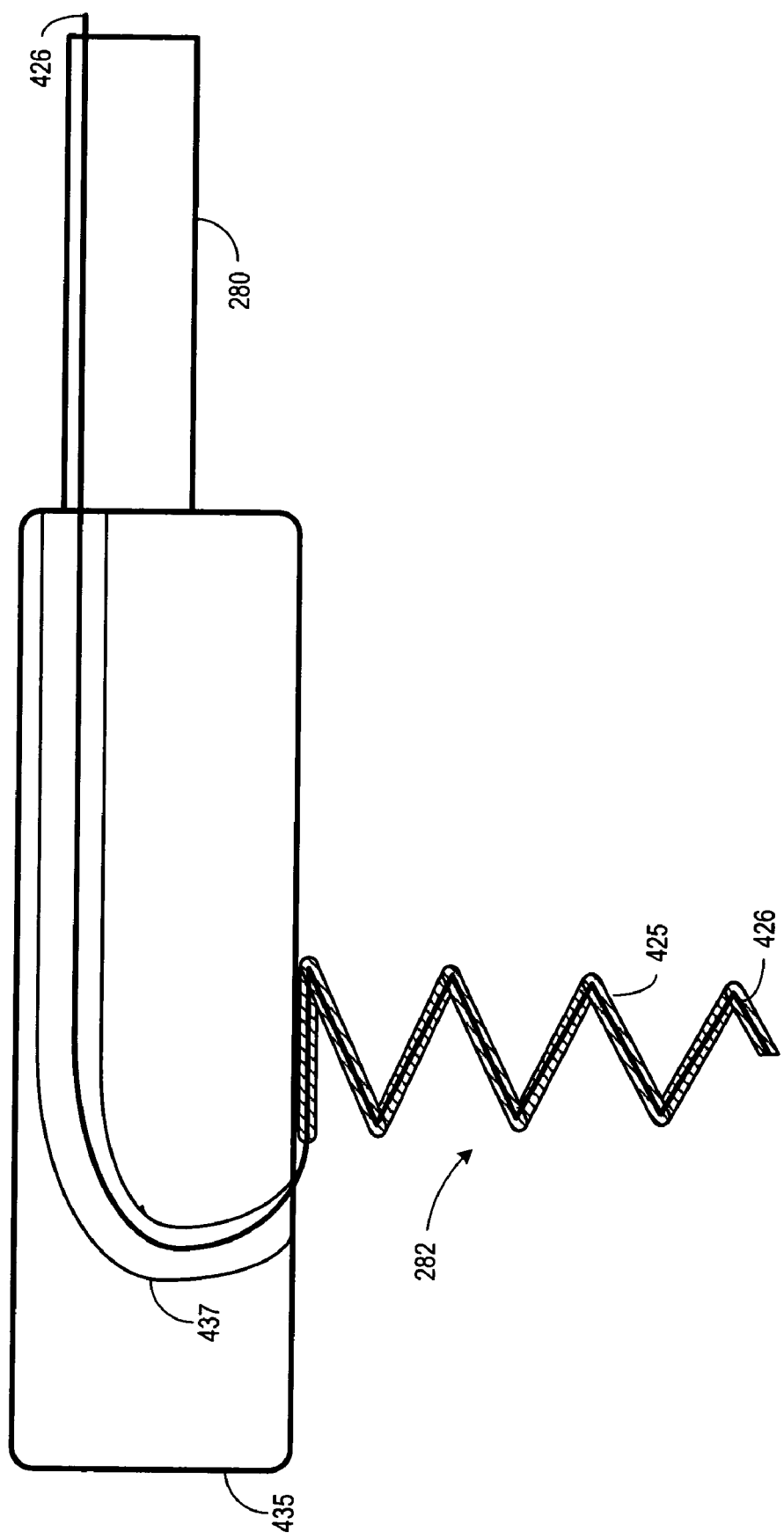
FIG. 4 illustrates another embodiment of a lead having a coated helical fixation arrangement in accordance with the present invention.

Referring to FIG. 4, the electrode 282 may be mounted to a lead 280 such as, for example, by mounting the electrode 282 to the distal end of the lead 280 such that electrode 282 extends perpendicularly to the longitudinal axis of the lead 280. The lead may be fixed, such as illustrated in FIGS. 3A and 3B, or may be extendable and retractable, as illustrated in FIG. 4. Extendable/retractable electrodes useful in accordance with the present invention are described in commonly owned U.S. Pat. Nos. 6,270,496 and 6,574,514, which are hereby incorporated herein by reference.

In FIG. 4, the electrode 282 includes a polymer layer 425 disposed as a coating on a wire 426 forming the electrode 282. In this configuration, the electrode 282 is pre-formed and biased to have a helical shape. The electrode 282 may be withdrawn into a head 435 when retracted. When properly positioned at the implant site, the electrode 282 may be extended through a guide or anvil 437, forming into the helical shape as the electrode 282 extends from the head 435, fixing it in place at the implant site.

It may be beneficial to provide polymer layer 425 with a pharmacological agent eluting capability to, for example, reduce swelling, aid in healing, and/or reduce pain. The helical electrode 420 (FIGS. 2, 3A, and 3B) or electrode 282 (FIG. 4) may include a polymer layer 425 or coating having a pharmacological eluting capability. Other systems and materials useful for drug delivery in accordance with the present invention are further described in commonly owned U.S. Pat. Nos. 4,819,662 and 6,361,780, which are hereby incorporated herein by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A cardiac lead, comprising:
   a lead body comprising one or more electrical conductors with associated insulators and having a proximal end and a distal end; and
   an epicardial electrode assembly situated at the distal end of the lead body, the electrode assembly comprising:
      a pacing electrode comprising an active fixation arrangement, the electrode electrically coupled to at least one of the electrical conductors; and
      a fluoropolymer coating or sleeve covering all of an electrically active surface of the active fixation arrangement sufficient in coverage to inhibit exit block development yet facilitate electrical stimulation of cardiac tissue.

2. The lead of claim 1, wherein the electrode assembly further comprises a polymeric coating disposed on at least the active fixation arrangement, and the fluoropolymer coating or sleeve is disposed over the polymeric coating.

3. The lead of claim 1, wherein the fluoropolymer coating or sleeve comprises a polytetrafluoroethylene coating or sleeve.

4. The lead of claim 1, wherein the fluoropolymer coating or sleeve comprises an ePTFE coating or sleeve.

5. The lead of claim 1, further comprising a steroid eluting sleeve disposed on the active fixation arrangement.

6. A cardiac lead, comprising:
   a lead body comprising one or more electrical conductors with associated insulators and having a proximal end and a distal end;
   a fixation arrangement that fixes the lead to tissue; and
   an epicardial electrode assembly situated at the distal end of the lead body, the electrode assembly comprising:
      a pacing electrode electrically coupled to at least one of the electrical conductors; and
      a fluoropolymer coating or sleeve provided on all of an electrically active surface of the electrode sufficient in coverage to inhibit exit block development yet facilitate electrical stimulation of cardiac tissue.

7. The lead of claim 6, wherein the electrode assembly further comprises a polymeric coating disposed on the electrode, and the fluoropolymer coating or sleeve is disposed over the polymeric coating.

8. The lead of claim 6, wherein the fluoropolymer coating or sleeve comprises a polytetrafluoroethylene coating or sleeve.

9. The lead of claim 6, wherein the fluoropolymer coating or sleeve comprises an ePTFE coating or sleeve.

10. The lead of claim 6, further comprising a steroid eluting sleeve disposed on the electrode.

11. The lead of claim 6, wherein the fixation arrangement comprises an acute fixation arrangement.

12. The lead of claim 6, wherein the fixation arrangement comprises a helical fixation arrangement.

13. The lead of claim 6, wherein the fixation arrangement comprises a chronic fixation arrangement.

14. A cardiac lead, comprising:
   a lead body comprising one or more electrical conductors with associated insulators and having a proximal end and a distal end; and
   an endocardial electrode assembly situated at the distal end of the lead body, the electrode assembly comprising:
      a pacing electrode comprising an active fixation arrangement, the electrode electrically coupled to at least one of the electrical conductors; and
      a fluoropolymer coating or sleeve provided on all of an electrically active surface of the active fixation arrangement sufficient in coverage to inhibit exit block development yet facilitate electrical stimulation of cardiac tissue.

15. The lead of claim 14, wherein the electrode assembly further comprises a polymeric coating disposed on at least the active fixation arrangement, and the fluoropolymer coating or sleeve is disposed over the polymeric coating.

16. The lead of claim 14, wherein the fluoropolymer coating or sleeve comprises a polytetrafluoroethylene coating or sleeve.

17. The lead of claim 14, wherein the fluoropolymer coating or sleeve comprises an ePTFE coating or sleeve.

18. The lead of claim 14, further comprising a steroid eluting sleeve disposed on the active fixation arrangement.

19. A cardiac lead, comprising:
   a lead body comprising one or more electrical conductors with associated insulators and having a proximal end and a distal end; and
   an endocardial electrode assembly situated at the distal end of the lead body, the electrode assembly comprising:
      at least one extendable/retractable pacing electrode, the electrode electrically coupled to at least one of the electrical conductors; and a fluoropolymer coating or sleeve provided on all of an electrically active surface of the electrode sufficient in coverage to inhibit exit block development yet facilitate electrical stimulation of cardiac tissue.

20. The lead of claim 19, wherein the electrode assembly further comprises a polymeric coating disposed on the electrode, and the fluoropolymer coating or sleeve is disposed over the polymeric coating.

21. The lead of claim 19, wherein the fluoropolymer coating or sleeve comprises a polytetrafluoroethylene coating or sleeve.

22. The lead of claim 19, wherein the fluoropolymer coating or sleeve comprises an ePTFE coating or sleeve.

23. The lead of claim 19, further comprising a steroid eluting sleeve disposed on the electrode.

24. A method of implanting a cardiac lead on a patient's heart, comprising:
    accessing, via a patient's chest cavity, an epicardial surface of the heart;
    moving an electrode assembly of the epicardial lead to an implant site on the epicardial surface, the electrode assembly comprising:
        a pacing electrode comprising an active fixation arrangement; and
        a fluoropolymer coating or sleeve provided on all of an electrically active surface of the active fixation arrangement sufficient in coverage to inhibit exit block development yet facilitate electrical stimulation of cardiac tissue; and
    implanting the electrode into myocardial tissue at the implant site by use of the active fixation arrangement.

25. The method of claim 24, wherein the active fixation arrangement comprises a helical shape imparted to the electrode.

26. The method of claim 24, wherein the electrode assembly further comprises a polymeric coating disposed on at least the active fixation arrangement, and the fluoropolymer coating or sleeve is disposed over the polymeric coating.

27. The method of claim 24, wherein the fluoropolymer coating or sleeve comprises a polytetrafluoroethylene coating or sleeve.

28. The method of claim 24, wherein the fluoropolymer coating or sleeve comprises an ePTFE coating or sleeve.

29. The method of claim 24, further comprising eluting a steroid at the implant site.

30. A method of implanting a cardiac lead in a patient's heart, comprising:
    accessing a chamber of the patient's heart;
    moving an electrode assembly of the endocardial lead to an implant site in the heart chamber, the electrode assembly comprising:
        a pacing electrode comprising an active fixation arrangement; and
        a fluoropolymer coating or sleeve provided on all of an electrically active surface of the active fixation arrangement sufficient in coverage to inhibit exit block development yet facilitate electrical stimulation of cardiac tissue; and
    implanting the pacing electrode into myocardial tissue at the implant site by use of the active fixation arrangement.

31. The method of claim 30, wherein the active fixation arrangement comprises a helical shape imparted to the electrode.

32. The method of claim 30, wherein the electrode assembly further comprises a polymeric coating disposed on at least the active fixation arrangement, and the fluoropolymer coating or sleeve is disposed over the polymeric coating.

33. The method of claim 30, wherein the fluoropolymer coating or sleeve comprises a polytetrafluoroethylene coating or sleeve.

34. The method of claim 30, wherein the fluoropolymer coating or sleeve comprises an ePTFE coating or sleeve.

35. The method of claim 30, further comprising eluting a steroid at the implant site.

* * * * *